United States Patent
Arakawa et al.

[11] Patent Number: 6,120,866
[45] Date of Patent: Sep. 19, 2000

[54] RE-PEELING PRESSURE-SENSITIVE ADHESIVE TAPE OR PRESSURE-SENSITIVE ADHESIVE, AND FASTENING SYSTEM USING THE SAME

[75] Inventors: Masaaki Arakawa; Katsumi Hori; Kazuhisa Maeda, all of Osaka, Japan

[73] Assignee: Nitto Denko Corporation, Osaka, Japan

[21] Appl. No.: 08/692,467

[22] Filed: Aug. 6, 1996

[30] Foreign Application Priority Data

Aug. 7, 1995 [JP] Japan .................................. 7-201048
Oct. 23, 1995 [JP] Japan .................................. 7-274054

[51] Int. Cl.[7] ...................................................... C09J 7/02
[52] U.S. Cl. .......................................... 428/40.1; 428/355
[58] Field of Search ...................... 428/355 BL, 355 AC, 428/355 RA, 40.1

[56] References Cited

U.S. PATENT DOCUMENTS 5,591,498  1/1997  Arakawa ................................ 428/343

FOREIGN PATENT DOCUMENTS 0306232A  3/1989  European Pat. Off. .
0683216A  11/1995  European Pat. Off. .

*Primary Examiner*—Jenna Davis
*Attorney, Agent, or Firm*—Sughrue, Mion, Zinn, Macpeak & Seas, PLLC

[57] ABSTRACT

A re-peeling pressure-sensitive adhesive or a re-peeling pressure-sensitive adhesive tape satisfying four conditions, besides (3) and (4), (1) and (2) or (1') and (2'): (1) the average releasing force in each releasing rate in the case of releasing at a releasing rate of from 10 to 100 meters/minute is from 50 to 1,000 g/25 mm, (2) the difference between the maximum value and the minimum value of the releasing force of the releasing chart pattern obtained by the release in (1) is not larger than ⅔ of the average releasing force or not larger than 500 g/25 mm, (1') the average releasing force in each releasing rate in the case of releasing at a releasing rate of from 1 meter/minute to 50 meters/minute is from 100 g/25 mm to 1,000 g/25 mm, (2') in the relation between the releasing force and the releasing rate after adhering to an adherend and preserving, the peak of the releasing force does not exist in the range of the releasing rate of not higher than 50 meters/minute, (3) the rolling initial tacking force is from 30 to 800 g/25 mm, and (4) the retentive force is at least 15 minutes under a load of 500 g. The pressure-sensitive adhesive and pressure-sensitive adhesive tape can be repeatedly adhered to or peeled from an adherend such as a paper diaper without breaking the adherend.

12 Claims, 3 Drawing Sheets

RE-PEELING PRESSURE-SENSITIVE ADHESIVE TAPE OR PRESSURE-SENSITIVE ADHESIVE, AND FASTENING SYSTEM USING THE SAME

FIELD OF THE INVENTION

The present invention relates to a re-peeling pressure-sensitive adhesive tape or a re-peeling pressure-sensitive adhesive, which can be repeatedly re-adhered and released many times for various kinds of adherends such as thin-layer films or sheets, nonwoven fabrics, woven fabrics, etc., and particularly for the foregoing very soft or low-strength adherends without breaking or damaging the adherends even when releasing is repeatedly carried out while it enables adhering and fixing with a sufficient adhesive force and a sufficient retentive force. Also, the invention relates to a fastening system using the re-peeling pressure-sensitive adhesive tape or the pressure-sensitive adhesive.

In addition, the re-peeling pressure-sensitive adhesive tape or pressure-sensitive adhesive of the present invention can be suitably used on the surface of the adherend described above when the adherend is reinforced by applying, for example, a plastic film or a pressure-sensitive adhesive tape to the back surface thereof.

There is no particular restriction on the practical uses of the re-peeling pressure-sensitive adhesive tape and pressure-sensitive adhesive of this invention but they are used, for example, as fixing tapes of various kinds of sanitary absorptive articles such as fastening tapes of paper diapers, package fixing tapes of sanitary napkins, etc.; light packaging of foods, etc., fixing tapes of garbage bags, surface protective tapes, etc.

BACKGROUND OF THE INVENTION

Various kinds of re-peeling pressure-sensitive adhesives and pressure-sensitive adhesive tapes are known, typically, for example, a Post-it (trade name, made by Minnesota Mining and Manufacturing Company) type is known, and such a type of re-peeling pressure-sensitive adhesive is very excellent in the re-peeling property. However, since such a re-peeling pressure-sensitive adhesive is for a temporary fixing function attaching importance to the re-peeling property and is not for fixing and sealing by adhering and fixing to various adherends, the re-peeling pressure-sensitive adhesive is insufficient in the point of the adhesive force or the retentive force and thus, for example, cannot be used as a fixing tape such as a fastener tape for paper diapers. That is, when such a type of pressure-sensitive adhesive tape is used for, a paper diaper, although the back sheet of the paper diaper as an adherend is not broken owing to the good re-peeling property but since the adhesive force, the retentive force, the initial tacking force, etc., are insufficient, there is a problem that the leakage of filth, etc., occurs by detaching or slipping of the tape.

On the other hand, as a fastener tape for disposable paper diaper, various pressure-sensitive adhesive compositions are known and, for example, for aiming that the releasing force shows the maximum force at a specific releasing rate, a pressure-sensitive adhesive composition comprising an A-B-A block copolymer such as a styrene-isoprene-styrene block copolymer, etc., a solid and liquid tackiness-imparting resins, and a terminal block reinforcing resin is proposed in JP-A-1-95175 (the term "JP-A" as used herein means an "unexamined published Japanese patent application").

However, when such a pressure-sensitive adhesive composition is used for, a fastener tape for a disposable paper diaper, although the tape is reluctant to detach owing to the large retentive force thereof, since the adhesive force (releasing force) in the rate range that a man peels a tape is too large, there is a problem that when, in particular, the back sheet of the paper diaper is composed of a very thin plastic film, the back sheet is broken at releasing the tape. Furthermore, there are other problems that after sticking the pressure-sensitive adhesive tape, by the passage of time for storing or by the temperature increase, etc., the adhesive force to the back sheet (adherend) is greatly increased as compared with the initial adhesive force, and in particular, since the releasing force becomes highest when the tape is released at a high rate, thereby causing some problems that the tape becomes reluctant to be released, the back sheet is broken, and the adhesive residue remains.

Also, when, in particular, releasing of the pressure-sensitive adhesive tape is carried out at a rate higher than the releasing rate at which the releasing force shows the peak, there are problems that a phenomenon of the vibration breakdown where the releasing force is periodically increased and decreased occurs, even when the maximum releasing force is below the breaking strength of the adherend, the concentration of stress is liable to occur at a point of the adherend and the back sheet is broken.

SUMMARY OF THE INVENTION

The present invention has been made for solving the conventional problems described above and the object of this invention is to provide a re-peeling pressure-sensitive adhesive tape or a re-peeling pressure-sensitive adhesive and a fastening system using them, which can repeatedly re-adhere and re-peel many times without breaking and damaging adherends even repeatedly carrying out re-peeling after passage of time in spite of having a sufficient adhesive force and a sufficient retentive force by designing a re-peeling pressure-sensitive adhesive simultaneously satisfying plural specific physical properties.

That is, according to a first aspect of the present invention, there is provided a re-peeling pressure-sensitive adhesive tape or pressure-sensitive adhesive, which can be freely adhered to an adherend and can be repeatedly adhered and re-peeled without breaking the adherend, wherein said pressure-sensitive adhesive tape or pressure-sensitive adhesive satisfies all the following conditions;

(1) the average releasing force in each releasing rate in the case of releasing at a releasing rate of from 10 meters/minute to 100 meters/minute is from 50 g/25 mm to 1,000 g/25 mm, (2) the difference between the maximum value and the minimum value of the releasing force of the releasing chart pattern (the graph showing the releasing force to the change of time) obtained by the release in (1) is not larger than $\frac{2}{3}$ of the average releasing force or not larger than 500 g/25 mm, (3) the rolling initial tacking force is from 30 g/25 mm to 800 g/25 mm, and (4) the retentive force is at least 15 minutes under a load of 500 g.

According to a second aspect of the present invention, there is also provided a re-peeling pressure-sensitive adhesive tape or pressure-sensitive adhesive, which can be freely adhered to an adherend and can be repeatedly adhered and re-peeled without breaking the adherend, wherein said pressure-sensitive adhesive tape or pressure-sensitive adhesive satisfies all the following conditions;

(1) the average releasing force in each releasing rate in the case of releasing at a releasing rate of from 1 meter/ minute to 50 meters/minute is from 100 g/25 mm to 1,000 g/25 mm, (2) in the relation between the releasing force and the releasing rate after adhering to an adherend and preserving, the peak of the releasing force does not exist in the range of the releasing rate of not higher than 50 meters/minute, (3) the rolling initial tacking force is from 30 g/25 mm to 800 g/25 mm, and (4) the retentive force is at least 15 minutes under a load of 500 g.

DETAILED DESCRIPTION OF THE INVENTION

Then, the present invention is described in detail.

First the 1st aspect of the present invention described above is described in detail.

In the re-peeling pressure-sensitive adhesive of the present invention and the re-peeling pressure-sensitive adhesive tape obtained by forming the re-peeling pressure-sensitive adhesive on an arbitrary substrate (hereinafter, they are sometimes referred to simply as a re-peeling pressure-sensitive adhesive, etc.), first, (1) it is necessary to be designed such that the releasing force in the case of releasing the pressure-sensitive adhesive tape from an adherend at a releasing rate of from 10 meters/minute to 100 meters/minute becomes from 50 g/25 mm to 1,000 g/25 mm, and preferably the average releasing force in each releasing rate in the case of releasing at a releasing rate of from 10 meters/minute to 50 meters/minute becomes 100 g/25 mm to 700 g/25 mm.

If the average releasing force is too small, although the tape can be easily released, the tape is inferior in the retentive force and there is possibility that the tape is detached from the adherend, while if the average releasing force is too large, although the tape is reluctant to be detached, the tape is reluctant to be released and the adherend is damaged.

Figure 1:
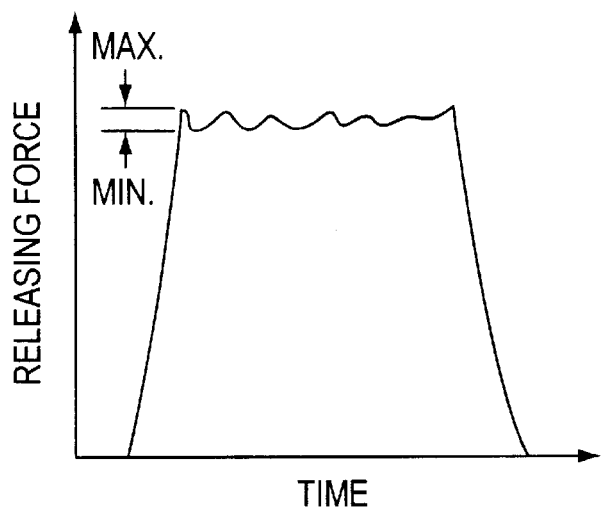
FIG. 1 is a schematic view showing an example of the release chart pattern in the releasing test of the re-peeling pressure-sensitive adhesive tape of the present invention and an adherend.

In this invention, the average releasing force is as follows. That is, an adherend is stuck to a stainless steel plate with a double faced pressure-sensitive adhesive tape at room temperature (usually 23° C.), the re-peeling pressure sensitive adhesive tape of this invention is adhered to the adherend by reciprocating once a roller of 2 kg, immediately thereafter, peeling adhesive force in the direction of 180 degree at a predetermined peeling rate is measured, and the average releasing force is calculated from the average value of the maximum value 10 points (10 points of the maximum values in a larger order) and the minimum value 10 points (10 points of the minimum values in a smaller order) in the releasing chart pattern (the graph showing the releasing force to the change of time) obtained as shown in FIG. 1.

In the re-peeling pressure-sensitive adhesive, etc., of the present invention, furthermore, (2) it is necessary to be designed such that the difference between the maximum value and the minimum value of the releasing force of the releasing chart pattern obtained from the release at the predetermined releasing rate described above becomes not larger than ⅔ of the average releasing force defined described above or not larger than 500 g/25 mm, and preferably not larger than ½ of the average releasing force or from 100 g/25 mm to 300 g/25 mm. The terminology "the difference between the maximum value and the minimum value" as used herein means the value obtained by subtracting the average value of the minimum value 10 points from the average value of the maximum value 10 points.

If the difference between the maximum value and the minimum value of the releasing force is over ⅔ of the average releasing force or is over 500 g/25 mm, the vibration at releasing the re-peeling pressure-sensitive adhesive tape becomes undesirably large, whereby there is a possibility that the adherend is broken by the vibration.

In the re-peeling pressure-sensitive adhesive, etc., of the present invention, furthermore, (3) it is necessary that the rolling initial tacking force defined below is from 30 g/25 mm to 800 g/25 mm, and preferably from 50 g/25 mm to 500 g/25 mm. If the rolling initial tacking force is less than 30 g/25 mm, the adhesive force is insufficient and the re-peeling pressure-sensitive adhesive tape is liable to be detached, while if the rolling initial tacking force is over 800 g/25 mm, there is a possibility that the adherend is broken.

In this invention, the rolling initial tacking force is obtained by the following method.

Figure 2:
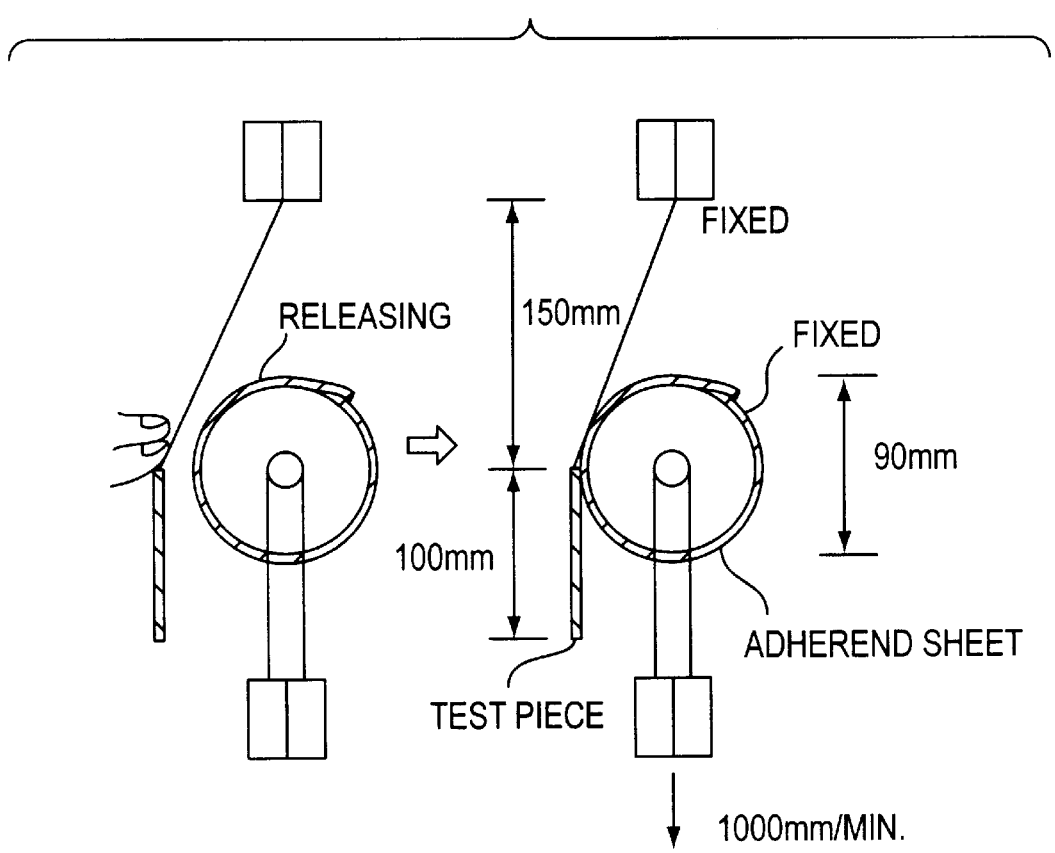
FIG. 2 is a schematic view showing an embodiment of the measurement method of a rolling initial tacking force in this invention.

First, as shown in FIG. 2, an adherend sheet is wound round a roll having a diameter of 90 mm and a width of 50 mm and the adherend sheet was fixed at the end only. Then, a test piece or tape (length 100 mm, width 25 mm) is suspended by hand and the test piece is released from the hand and adhered to the adherend. Then, the roll is moved downward at the pulling rate of 1,000 mm/minute, and the maximum adhesive force measured in this case is defined as the rolling initial tacking force in the present invention. In addition, the measurement condition is under the atmosphere of 23° C. and 60% RH.

In the re-peeling pressure-sensitive adhesive, etc., of the present invention, moreover (4) it is necessary that the retentive force thereof is at least 15 minutes, and preferably at least 30 minutes under a load of 500 g. It is preferable that the retentive force is as long as possible and, for example, at least 4 hours under a load of 500 g at 23° C. can be defined as a target level. In this case, if the retentive force is less than 15 minutes, the adhesive force of the pressure-sensitive adhesive tape and the adherend is easily weakened by an outer force of the shearing direction, whereby the tape is finally detached. For example, when such a pressure-sensitive adhesive tape is used as a fastening system for a diaper, detaching of the pressure-sensitive tape causes the undesirable leakage of a filth.

In this case, the retentive force means as follows. That is, an adherend is stuck to a stainless steel plate with a double-faced pressure-sensitive adhesive tape at room temperature (usually 23° C.), and the re-peeling pressure-sensitive adhesive tape having a width of 25 mm of the present invention is adhered on the adherend by reciprocating once a roller of 2 kg. The size of the adhered portion of the tape is 25×25 mm and the other portion on the same side is covered with a film so as not to adhere to the adherend. Then, the stainless steel having the adherend adhered with the tape is placed such that the adhered surface between the adherend and the tape is vertical, and a load of 500 g is hung on the end of the non-adhered portion of the tape. The time at which the tape falls is defined as the retention force.

Furthermore, in the re-peeling pressure-sensitive adhesive, etc., of the present invention, it is preferred that the maximum releasing force (the largest value obtained in the releasing chart pattern) in the releasing rate of from 50 meters/minute to 100 meters/minute is not larger than the breaking strength of an adherend. In this case, the releasing force is same as defined above. When the releasing force is over the breaking strength of an adherend, there is a possibility that at releasing the pressure-sensitive tape from an adherend, the adherend is damaged.

In this case, the breaking strength of an adherend means the strength at the case of pulling in the MD direction (machine direction) or the TD direction (traverse direction), preferably in the direction of adhering the pressure-sensitive adhesive tape to an adherend and releasing the tape, at a rate of 300 meters/minute and fracturing the adherend.

Also, the re-peeling pressure-sensitive adhesive tape of the present invention is further preferred to be designed such that the adhesive force (releasing force) at the case of re-peeling the pressure-sensitive adhesive, the pressure-sensitive adhesive tape, etc., after adhering the pressure-sensitive adhesive or the pressure-sensitive adhesive tape to an adherend and preserving them is increased not more than 4 times, and preferably from about 1.2 to 3.0 times only the initial adhesive force. When the increase of such an adhesive force is over 4 times the initial adhesive force, the adhesive force (releasing force) is too strong and there is a possibility that an adherend such as, the back sheet of paper diaper is broken. In this case, the initial adhesive force is an adhesive force in the case of releasing the pressure-sensitive adhesive tape within about 30 minutes after adhering the tape. Also, the adhesive force at re-peeling is a 180° peeling adhesive force (pulling rate 300 mm/minute) after adhering an adherend and the pressure-sensitive adhesive tape and preserving for one day at 50° C.

Then, the second aspect of the present invention described above is described in detail.

In the re-peeling pressure-sensitive adhesive in the second aspect of the present invention and the re-peeling pressure-sensitive adhesive tape obtained by forming the re-peeling pressure-sensitive adhesive on an arbitrarily substrate (hereinafter, they are sometimes referred to simply as a re-peeling pressure-sensitive adhesive, etc.), first, (1) it is necessary to be designed such that the releasing force in the case of releasing the pressure-sensitive adhesive tape from an adherend at a releasing rate of from 1 meter/minute to 50 meters/minute becomes from 100 g/25 mm to 1,000 g/25 mm.

If the average releasing force is too small, although the tape can be easily released, the tape is inferior in the retentive force and there is possibility that the tape is detached from the adherend, while if the average releasing force is too large, adherend is damaged or if not, it becomes very difficult to release the tape.

In the re-peeling pressure-sensitive adhesive, etc., in the second aspect of the present invention, it is further preferred that the average releasing force at each releasing rate in the case of releasing at a releasing rate of from 1 meter/minute to 50 meters/minute is at least 100 g/25 mm and the maximum releasing force is not larger than the breaking strength of the adherend. When the releasing force of the pressure-sensitive tape is over the breaking strength of the adherend, there is a possibility that the adherend is damaged at releasing the pressure-sensitive adhesive tape from the adherend.

In this case, the breaking strength of an adherend means the strength at the case of pulling in the MD direction or the TD direction, preferably in the direction of adhering the pressure-sensitive adhesive tape to an adherend and releasing the tape, at a rate of 300 meters/minute and fracturing the adherend.

In the re-peeling pressure-sensitive adhesive, etc., of this invention, furthermore, (2) it is important that in the relation of the releasing force and the releasing rate after adhering to an adherend and preserving (defined hereinbelow), the releasing force is increased with the releasing rate and the peak of the releasing force does not exist in the range of the releasing rate of 50 meters/minute or less.

If the peak of the releasing force exists in the range of the releasing rate of 50 meters/minute or less, when releasing of the tape is carried out at a rate higher than the releasing rate showing the peak, a phenomenon of a vibration destruction where the releasing force increases and decreases periodically occurs and even when the maximum releasing force is below the breaking strength of the adherend, the concentration of stress is liable to occur at one point of the adherend to undesirably fracture the adherend.

In this case, the releasing force is the value obtained by sticking an adherend to a stainless steel plate with a double faced pressure-sensitive adhesive tape at room temperature (usually 23° C.), adhering the re-peeling pressure-sensitive adhesive tape of the present invention to the adherend by reciprocating once a roller of 2 kg, and immediately measuring the peeling adhesive force in the direction of 180 degree at a predetermined releasing rate.

Also, the releasing force after adhering and preserving is the value obtained by adhering the re-peeling pressure-sensitive adhesive tape to an adherend as described above, preserving them for one day at 50° C., then allowing to lower the temperature to room temperature, and after allowing to stand for 2 hours, measuring the peeling adhesive force in the 180 degree direction. Also, the average releasing force means the releasing force calculated from the average value of the maximum value 10 points and the minimum value 10 points in the releasing chart pattern (the graph showing the releasing force to the change of time) obtained, and the maximum releasing force is the largest value in the releasing chart pattern. Also, the peak of the releasing force is the maximum value of the average releasing force in each releasing rate.

In the re-peeling pressure-sensitive adhesive, etc., of the second aspect of the present invention, furthermore, (3) it is necessary that the rolling initial tacking force defined in the first aspect of the invention above is from 30 g/25 mm to 800 g/25 mm, and preferably from 50 g/25 mm to 500 g/25 mm. If the rolling initial tacking force is less than 30 g/25 mm, the releasing force is insufficient and the re-peeling pressure-sensitive tape is liable to be detached, while if the rolling initial tacking force is over 800 g/25 mm, there is a possibility that the adherend is broken.

In the re-peeling pressure-sensitive adhesive, etc., of the 2nd aspect of the present invention, moreover (4) it is necessary that the retentive force thereof is at least 15 minutes, and preferably at least 30 minutes under a load of 500 g. It is preferable that the retentive force is as long as possible and, for example, at least 4 hours under a load of 500 g at 23° C. can be defined as a target level. In this case, if the retentive force is less than 15 minutes, the adhesive force of the pressure-sensitive adhesive tape and the adherend is easily weakened by an outer force of the shearing direction, whereby the tape is finally detached. For example, when such a pressure-sensitive adhesive tape is used as a fastening system for a diaper, detaching of the pressure-sensitive tape undesirably causes the leakage of a filth. In this case, the retentive force is the time measured by the method described above in relation to the first aspect of the present invention.

There is no particular restriction on each composition of the re-peeling pressure-sensitive adhesive in the first aspect or the second aspect of the present invention if the compositions simultaneously satisfy at least the plural conditions (1) to (4) described above and, for example, there are a synthetic rubber series pressure-sensitive adhesive and an acrylic pressure-sensitive adhesive.

Practically, it is desirable that the synthetic rubber series pressure-sensitive adhesive contains an elastomer which is the block copolymer composed of at least a polymer block A mainly composed of a vinyl aromatic compound and polymer block B mainly composed of a conjugated diene compound. In this case, as the particularly preferable elastomer, for example, styrene series synthetic block copolymers such as a styrene-isoprene-styrene block copolymer (SIS), a styrene-butadiene-styrene block copolymer (SBS), the hydrogenated type copolymers of them (SIPS, SEBS), etc., are used singly or as a mixture thereof.

In the present invention, as the foregoing elastomer, the block copolymer composed of the polymer block A mainly composed of a vinyl aromatic compound and the polymer block B mainly composed of a conjugated diene compound, wherein the content of the block A (styrene) is at least 17% by weight and the coupling ratio is at least 50% is preferably used. Particularly preferably, there are the block copolymer, wherein the content of the block A (styrene) is from 17 to 50% by weight and the coupling ratio is from 70 to 100% and the branched or radial block copolymer having at least 3 terminal polymer block As.

In this case, the block copolymer is generally composed of a block polymer called a triblock having at least 2 terminal polymer blocks induced from a vinyl aromatic compound and at least one intermediate polymer block induced from a conjugated diene compound, a homopolymer of a conjugated diene or a vinyl aromatic compound, and a diblock bonded with a block induced from one vinyl aromatic compound. The ratio of the triblock to the total blocks is called coupling ratio.

Specific examples of the elastomer, are, for example, Kraton G-1657 (trade name, made by Shell Kagaku K.K.; styrene-ethylene-butadiene-styrene block copolymer, styrene content: 30% by weight, coupling ratio: 65%), SH-108 (trade name, made by Nippon Zeon Co., Ltd.; styrene-isoprene-styrene block copolymer, styrene content: 25% by weight, coupling ratio: 60%, branched), Quintac 3450 (trade name, made by Nippon Zeon Co., Ltd.; styrene-isoprene-styrene block copolymer, styrene content: 19% by weight, coupling ratio: 70%), Vector V-4111D (trade name, made by Tornex Co.; styrene-isoprene-styrene block copolymer, styrene content: 18% by weight, coupling ratio: higher than 99%), Vector V-4211D (trade name, made by Tornex Co.; styrene-isoprene-styrene block copolymer, styrene content: 30% by weight, coupling ratio: not less than 99%), RP-6405 (trade name, made by Shell Kagaku K.K.; styrene-isoprene-styrene block copolymer, styrene content: 30% by weight, coupling ratio: 80%), RP-6404 (trade name, made by Shell Kagaku K.K.; styrene-isoprene-styrene block copolymer, styrene content: 30% by weight, coupling ratio: 70%), Kraton D-1114X (trade name, made by Shell Kagaku K.K.; styrene-isoprene-styrene block copolymer, styrene content: 19% by weight, coupling ratio: 100%), and Kraton D-1320X (trade name, made by Shell Kagaku K.K.; styrene-isoprene-styrene block copolymer, styrene content: 10% by weight, coupling ratio: 90%), although the elastomer being used in the present invention is not limited to them.

Also, in the case of the acryl series pressure-sensitive adhesive, an emulsion series pressure-sensitive adhesive and a solvent series pressure-sensitive adhesive are used. In the case of the emulsion series pressure-sensitive dhesive, the adhesive having a high cohesive force is particularly preferred and in the case of the solvent series pressure-sensitive adhesive, acrylic acid, butyl acrylate, 2-ethylhexyl acrylate, or a blend of them is preferred. Furthermore, in the case of using the re-peeling pressure-sensitive adhesive for sanitary materials or food packaging, from the point that an odor and a safety are important, it is preferred that unreacted acryl monomers are less and it is also preferred that the copolymer has a polymerization ratio of at least 93% and is further crosslinked.

The re-peeling pressure-sensitive adhesive of this invention can be compounded with a tackiness-imparting resin if necessary and the compounding amount, it is desirable that the compounding amount of the tackiness-imparting resin is from 20 to 200 parts by weight, and more preferably from 30 to 180 parts by weight to 100 parts by weight of the polymer component. If the compounding amount of the tackiness-imparting resin is less than 20 parts by weight, the modulus of elasticity is lowered with the passage of time or the increase of temperature and the adhesive force is lowered, or there are problems that the tackiness of such a pressure-sensitive adhesive is originally weak and the adhesive force is small. n the other hand, if the compounding amount of the tackiness-imparting resin is over 200 parts by weight, there is a problem that the pressure-sensitive adhesive is inferior in the tackiness and the adhesive property in a low-temperature range.

There is no particular restriction on such a tackiness-imparting resin if the resin is in a solid state or a liquid state at normal temperature but from the purpose of restraining the increase of the adhesive force and from the point of not lowering the cohesive force and the elastic modulus of the pressure-sensitive adhesive, in the case of solid, it is preferred that the softening point thereof is from about 60 to 150° C., and particularly from 70 to 100° C.

For example, petroleum series resins such as Marukarez series (trade name, made by Maruzen Petrochemical Co., Ltd.), the Escorez series (trade name, made by Tornex Co.), etc.; alicyclic resins such as Arkon M series (trade name, made by Arakawa Chemical Industry Ltd.), etc.; and terpene series resins such as Clearon series (trade name, made by Yasuhara Chemical Co., Ltd.) can be used singly or as a mixture thereof.

Also, the foregoing re-peeling pressure-sensitive adhesive can contain, if necessary, an antioxidant, a softener such as a paraffin oil, a coloring agent and filler (such as titanium white, zinc white, calcium carbonate, talc, white mica, and a pigment), etc.

Furthermore, since the pressure-sensitive adhesive of this kind can be easily hot melted, the adhesive has the advantages that the productivity is increased and occurrence of an environmental pollution can be prevented as compared with solvent type adhesives.

Also, there is no particular restriction on the thickness of the pressure-sensitive adhesive layer as long as the layer satisfies all the properties defined in the present invention, but the thickness is usually from about 20 $\mu$m to 100 $\mu$m, and preferably from about 30 $\mu$m to 70 $\mu$m.

Figure 3:
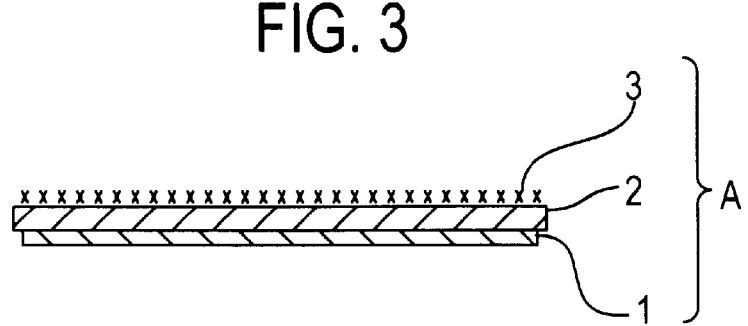
FIG. 3 is a cross sectional view showing an embodiment of the re-peeling pressure-sensitive adhesive tape of the present invention.

The re-peeling pressure-sensitive adhesive tape of the present invention can be constituted by only a pressure-sensitive adhesive layer but it is preferred to provide as a pressure-sensitive adhesive tape A or sheet composed of an appropriate substrate 2 having formed on one surface thereof the re-peeling pressure-sensitive adhesive layer 1 satisfying the specific properties of this invention as shown in FIG. 3. Furthermore, a back treatment layer 3 composed of a silicone series releasing agent may be formed on the other surface of the substrate as shown in FIG. 3.

There is no particular restriction on the foregoing substrate, but examples thereof include plastic films such as polyester series films, polyolefin series films (e.g, polyethylene, polypropylene, or the blend thereof) or a laminate thereof, and nonwoven fabrics.

Figure 4:
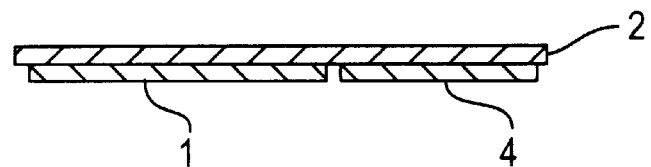
FIG. 4 is a cross sectional view showing other embodiment of the re-peeling pressure-sensitive adhesive tape of the present invention.

Also, as shown in FIG. 4, a pressure-sensitive tape composed of a substrate 2 having formed on one surface the re-peeling pressure-sensitive adhesive layer 1 of the present invention together with a pressure-sensitive adhesive layer 4 for fixing composed of a conventional pressure-sensitive adhesive can be prepared. The pressure-sensitive tape can be previously fixed to, for example, a paper diaper or other adherend with the pressure-sensitive adhesive layer 4 for fixing and the re-peeling pressure-sensitive adhesive layer 1 can be used as fastener tape which can be opened and closed with a hand.

Figure 5:
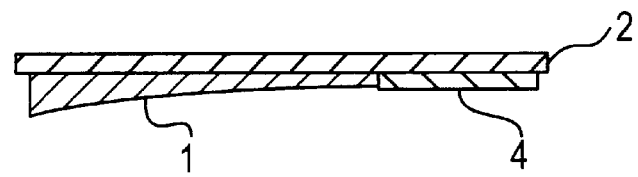
FIG. 5 is a cross sectional view showing still other embodiment of the re-peeling pressure-sensitive adhesive tape of the present invention.

Furthermore, as shown in FIG. 5, by changing the thickness of the re-peeling pressure-sensitive adhesive layer 1 such that the thickness becomes gradually thicker toward the end portion, peeling can be effected heavily at the beginning of releasing (low-rate releasing zone) and lightly at the end of releasing (high-rate releasing zone), which has the effect that the adherend can be reluctant to be broken and also since the release in the low-rate releasing zone is heavy, the pressure-sensitive tape becomes strong to the detaching such that the tape is gradually released.

The present invention also provides a fastening system that the foregoing re-peeling pressure-sensitive adhesive tape or re-peeling pressure-sensitive adhesive is re-peelably adhered to various adherends.

There is no particular restriction on the adherend being applied with the re-peeling pressure-sensitive adhesive tape or the re-peeling pressure-sensitive adhesive of the present invention but the pressure-sensitive adhesive tape or pressure-sensitive adhesive is suitably applied to a relatively small strength and, for example, they can be applied to an adherend having a breaking strength (as defined above) of from 0.02 kg/10 mm to 10 kg/10 mm, and preferably from 0.02 kg/10 mm to 5 kg/10 mm. Since the re-peeling pressure-sensitive adhesive of the present invention has the specific properties described above, the pressure-sensitive adhesive tape has the advantage that the pressure-sensitive adhesive adheres to an adherend having such a breaking strength and a relatively small strength and when the tape is re-peeled, and the adherend is not broken.

As specific examples of such an adherend, there are thin polyolefinic (polyethylene, polypropylene, etc.) films having a thickness of from 5 to 200 $\mu$m, polyolefinic non-woven or woven fabrics having a basis weight of from 5 to 200 g/m$^2$ or composite materials of them.

There is no particular restriction on the use of the re-peeling pressure-sensitive adhesive tape of the present invention but as the suitable uses, there are fixing tapes for absorptive articles and packaged articles. For example, there is a fastening system of a disposable diaper, wherein the re-peeling pressure-sensitive adhesive tape is used as a fastener tape for a paper diaper and the tape is used for adhering and fixing to the surface of the back sheet of a disposable diaper and re-peeling.

Figure 6:
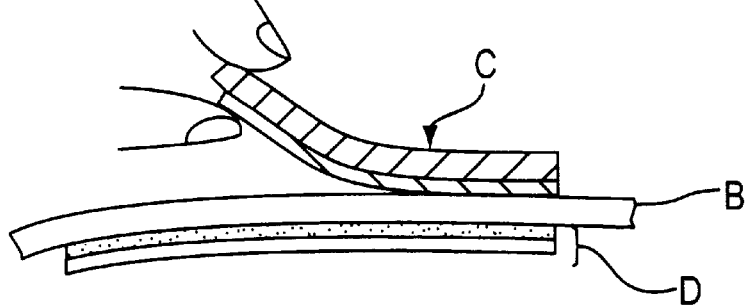
FIG. 6 is a cross sectional view showing an embodiment of the fastening system using the re-peeling pressure-sensitive adhesive tape of the present invention.
Figure 7:
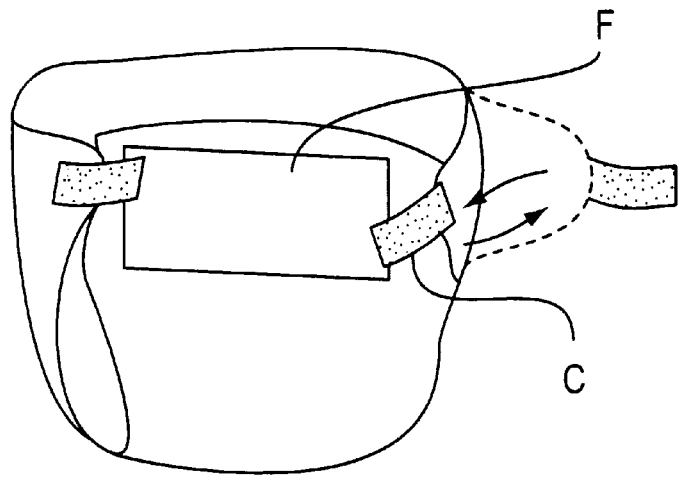
FIG. 7 is a schematic view showing other embodiment of the fastening system of a paper diaper using the re-peeling pressure-sensitive adhesive tape of the present invention.
Figure 8:
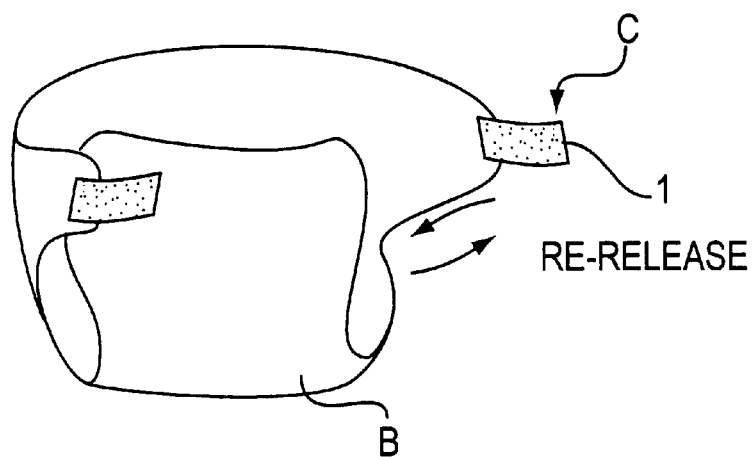
FIG. 8 is a schematic view showing still other embodiment of the fastening system of a paper diaper using the re-peeling pressure-sensitive adhesive tape of the present invention.

That is, in the case of using for the fastening system of a disposable diaper, as shown in FIG. 7 or FIG. 8, a so-called frontal tape (reinforcing film) F or a back sheet B becomes an adherend and the re-peeling pressure-sensitive adhesive 1 of this invention functions as a pressure-sensitive adhesive for a fastener tape C. However, if necessary, as shown in FIG. 6, a reinforcing tape D for showing the adhering position or for preventing breaking can be formed at the back surface of the back sheet B.

The back sheet which is an adherend in the fastening system of such a disposable diaper is usually a polyolefinic plastic film or sheet and, for example, a polyethylene film or a polypropylene film is used. Also, a composite material of the polyolefinic film and a paper, a cloth, a nonwoven fabric, etc., is preferably used. Also, as such a back sheet, a porous-type sheet having a moisture permeability can be used as such a back sheet. Also, as described above, if necessary, by sticking a reinforcing tape to the back surface of the back sheet or by coating a hot melt to the back surface thereof to form a composite structure with a constituting member such as a nonwoven fabric, the position at which the fastener tape is stuck is clarified and the strength can be increased, which is effective for preventing breaking of the back sheet.

Figure 9:
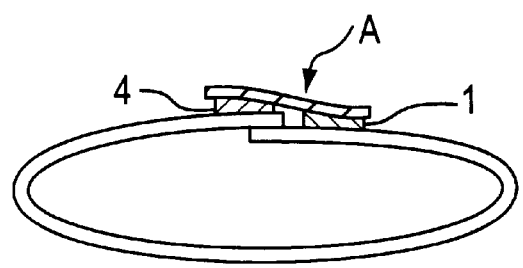
FIG. 9 is a schematic view showing an embodiment of the fastening system of a package using the re-leasing pressure-sensitive adhesive tape.

There is no restriction on the use of the re-peeling pressure-sensitive adhesive and the re-peeling pressure-sensitive adhesive tape of this invention, in addition to the fastening system of the disposable diapers described above, they can be used for, for example, fixing a package of a sanitary napkin (FIG. 9), fixing of package for foods, fixing of light package, and surface protection.

The re-peeling pressure-sensitive adhesive tape or re-peeling pressure-sensitive adhesive of the present invention can be adhered and fixed to various adherends such as thin films or sheets, non-woven fabrics, woven fabrics, etc., or further to very soft adherends or adherends having a weak strength with a sufficient adhesive force and retentive force, and when re-peeling is repeatedly carried out after passage of time, the adherends are not broken or damaged. Thus, they have a very practical advantage that re-adhering and re-peeling can be carried out repeatedly many times.

EXAMPLES

The following examples are intended to illustrate the present invention but not to limit the invention in any way. In addition, all parts in these examples, unless otherwise indicated, are by weight.

In the following examples and comparative examples, re-peeling pressure-sensitive tape as shown in FIG. 3 was obtained by forming on one surface of an oriented polypropylene (OPP) film of 40 μm in thickness the re-peeling pressure-sensitive adhesive layer having the composition and the thickness shown below and forming on the other surface a silicone back surface treating agent layer (coated amount: 0.5 g/m²).

Example 1-1

Thickness of pressure-sensitive adhesive layer: 40 μm

| | |
|---|---|
| Butyl Acrylate | 100 parts |
| Acrylic Acid | 10 parts |
| Antioxidant (Irganox 1010, trade name, made by Ciba Geigy Co., Ltd.) | 1 part |

Example 1-2

Thickness of pressure-sensitive adhesive layer: 40 μm

| | |
|---|---|
| Styrene-Ethylene-Butadiene-Styrene Copolymer (styrene content: 30% by weight, coupling ratio: 65%, linear, Kraton G-1657, made by Shell Kagaku K.K.) | 100 parts |
| Aliphatic Petroleum Series Resin (Clearon P-125, made by Yasuhara Chemical Industry Ltd.) | 30 parts |
| Liquid Terpene Series Resin (YS Resin, made by Yasuhara Chemical Co., Ltd.) | 5 parts |
| Antioxidant (Irganox 1010, made by Ciba Geigy Ltd.) | 1 part |

Example 1-3

Thickness of pressure-sensitive adhesive layer: 40 μm

| | |
|---|---|
| Styrene-Isoprene-Styrene Copolymer (styrene content: 25% by weight, coupling ratio: 60%, branched, SH-108, made by Nippon Zeon Co. Ltd.) | 100 parts |
| Hydrogenated Petroleum Series Resin (Arkon M-135, made by Arakawa Chemical Industry Ltd.) | 70 parts |
| Antioxidant (Irganox 1010, made by Ciba Geigy Ltd.) | 1 part |
| Paraffin Oil | 20 parts |

Comparative Example 1-1

Thickness of pressure-sensitive adhesive layer: 40 4μm

| | |
|---|---|
| 2-Ethylhexyl Acrylate | 100 parts |
| Acrylic Acid | 10 parts |
| Antioxidant (Irganox 1010, made by Ciba Geigy Ltd.) | 1 part |

Comparative Example 1-2

Thickness of pressure-sensitive adhesive layer: 15 μm

| | |
|---|---|
| Butyl Acrylate | 100 parts |
| Acrylic Acid | 10 parts |
| Antioxidant (Irganox 1010, made by Ciba Geigy Ltd.) | 1 part |

On the other hand, a mixture of 100 parts of low-density polyethylene and 110 parts of calcium carbonate was extruded by a T die and stretched to form a sheet of 40 μm in thickness to provide an adherend A.

By using the adherend A, the initial average releasing force, the average releasing force after heating (after adhering and preserving at 50° C. for 1 day), the difference of the maximum releasing force and the minimum releasing force in the releasing chart pattern, the rolling initial tacking force, and the retentive force of each of the re-peeling pressure-sensitive adhesive tapes obtained in the examples and the comparative examples described above were measured by the methods described above and the results are shown in Table 1-1.

In addition, the reason why 50° C.×1 day was adopted as the preserving condition is that since the condition of usually using the tape was near the body temperature (about 40° C.×1 day), the severer condition than the above condition was selected.

TABLE 1-1

| Example No. | Initial Average Releasing Force Releasing Rate | | Releasing Force After Heating Releasing Rate | | Difference Between Maximum Value and Minimum Value of Releasing Force | | Rolling Initial Tacking Force | Retentive Force |
|---|---|---|---|---|---|---|---|---|
| | 10 m/min. (g/25 mm) | 50 m/min. (g/25 mm) | 10 m/min. (g/25mni) | 50 m/min. (g/25 mm) | 10 m/min. (g/25 mm) | 50 m/min. (g/25 mm) | (g/25 mm) | (min.) |
| Example 1-1 | 120 | 170 | 180 | 250 | 110 | 130 | 390 | 30 |
| Example 1-2 | 150 | 210 | 230 | 380 | 120 | 140 | 80 | ≧200 |

TABLE 1-1-continued

| | Initial Average Releasing Force Releasing Rate | | Releasing Force After Heating Releasing Rate | | Difference Between Maximum Value and Minimum Value of Releasing Force | | Rolling Initial Tacking | Retentive |
|---|---|---|---|---|---|---|---|---|
| Example No. | 10 m/min. (g/25 mm) | 50 m/min. (g/25 mm) | 10 m/min. (g/25mni) | 50 m/min. (g/25 mm) | 10 m/min. (g/25 mm) | 50 m/min. (g/25 mm) | Force (g/25 mm) | Force (min.) |
| Example 1-3 | 180 | 280 | 260 | 320 | 150 | 180 | 120 | 60 |
| Comparative Example 1-1 | 80 | 190 | 160 | 230 | 120 | 160 | 20 | 14 |
| Comparative Example 1-2 | 40 | 90 | 100 | 150 | 60 | 90 | 40 | 5 |

Practical Using Test

Paper diapers each having a back sheet as adherend A obtained by adhering and fixing thereto each of the re-peeling pressure-sensitive adhesive tapes (the type of FIG. 4) obtained in the examples and the comparative examples were distributed to 15 mothers at 5 paper diapers per one mother, the practical usability was evaluated by the following standard, and the results are shown in Table 1-2.

A: Not less than 10 Persons in 15 persons evaluated as good.

B: Six to 9 Persons in 15 persons evaluated as good.

C: Not more than 5 persons in 15 persons evaluated as good.

TABLE 1-2

Practical Using Test

| Example No. | Releas- ability | Break- age of Sheet | Detach- ing of Tape | Initial Adhesive Property | Re- adhesive Property | Total Evalua- tion |
|---|---|---|---|---|---|---|
| Example 1-1 | A | A | A | A | A | A |
| Example 1-2 | A | A | A | A | A | A |
| Example 1-3 | A | A | A | A | A | A |
| Compara- tive Example 1-1 | A | A | C | A | B[1] | C |
| Compara- tive Example 1-2 | A | A | C | C[2] | C | C |

Note)
1: Unreliable
2: Too weak

Breaking Test of Adherend Sheet

Each of the re-peeling pressure-sensitive adhesive tapes obtained in the examples and the comparative examples was adhered to each of the following adherend sheets, the adhered adherend sheets directly after adhering under the atmosphere of 23° C. and the adhered adherend sheets after preserving for 12 hours under the conditions of 40° C. and 92% RH were prepared, and breaking test was carried out by releasing the re-peeling pressure-sensitive tape by a hand. The releasing rate in this case was from 20 to 100 meters/minute.

Also, the breaking strength was obtained by the method described above and the results are shown in Table 1-3.

Sheet A: The adherend A (thickness: 40 $\mu$m) used in the examples.

Sheet B: Thin type of sheet A (thickness: 20 $\mu$m).

Sheet C: Polyethylene/polyester composite fibrous nonwoven fabric (basis weight: 50 g/m$^2$).

Sheet D: Polypropylene nonwoven fabric (basis weight: 50 g/m$^2$).

Sheet E: Laminated type of sheet B and sheet D. (The pressure-sensitive tape is brought into contact with the sheet D side.)

Sheet F: Non-porous polyethylene film (thickness: 30 $\mu$m).

In addition, the result of the breaking test of each sheet was evaluated by the following standard.

A: Good
B: Elongation occurred
C: Broken

TABLE 1-3

| | Breaking | Breaking Test | | | |
|---|---|---|---|---|---|
| Sample of Adherend Sheet | Strength in MD Direction (kg/10 mm) | Example 1-1 | Example 1-2 | Example 1-3 | Compara- tive Example 1-1 |
| A | 1.0 | A | A | A | A |
| B | 0.5 | A | A | A | C |
| C | 0.8 | A | A | A | A |
| D | 0.7 | A | A | A | A |
| E | 1.5 | A | A | A | A |
| F | 0.8 | A | A | A | B |

In the following examples and comparative examples, each of re-peeling pressure-sensitive adhesive tapes as shown in FIG. 3 was obtained by forming one surface of an oriented polypropylene (OPP) film of 40 $\mu$m in thickness each of the re-peeling pressure-sensitive adhesives having the following compositions at a thickness of 40 $\mu$m and forming on the other surface thereof a silicone series back surface (coated amount: 0.5 g/m$^2$).

Example 2-1

| | |
|---|---|
| 2-Ethylhexyl Acrylate | 98 parts |
| Acrylic Acid | 2 parts |
| Rosin Series Resin (Super Ester A-125, made by Arakawa Chemical Industry Ltd.) | 10 parts |
| Isocyanate Series Crosslinking Agent (Coronate L, made by Nippon Polyurethane Industry Co., Ltd.) | 2 parts |

Example 2-2

| | |
|---|---|
| Styrene-Ethylene-Butadiene-Styrene Copolymer (styrene content: 30% by weight, coupling ratio: 65%, linear, Kraton G-1657, made by Shell Kagaku K.K.) | 100 parts |
| Petroleum Series Resin (Marukarez H-700F, made by Maruzen Petrochemical Co., Ltd.) | 30 parts |
| Liquid Terpene Series Resin (YS Resin, made by Yasuhara Chemical Co., Ltd.) | 5 parts |
| Antioxidant (Irganox 1010, made by Ciba Ceigy Ltd.) | 1 part |

Example 2-3

| | |
|---|---|
| Styrene-Isoprene-Styrene Copolymer (styrene content: 25% by weight, coupling ratio: 60%, branched, SH-108, made by Nippon Zeon Co., Ltd.) | 100 parts |
| Hydrogenated Terpene Series Resin (Clearon P-125, made by Yasuhara Chemical Industry Co., Ltd.) | 70 parts |
| Paraffin Oil | 20 parts |
| Antioxidant (Irganox 1010, made by Ciba Geigy Ltd.) | 1 part |

Comparative Example 2-1

| | |
|---|---|
| Styrene-Isoprene-Styrene Copolymer (styrene content: 15% by weight, coupling ratio: 85%, Kraton D-1107, made by Shell Kagaku K.K.) | 100 parts |
| Hydrogenated Petroleum Series Resin (Arkon M-135, Arakawa Chemical Industry Ltd.) | 70 parts |
| Antioxidant (Irganox 1010, made by Ciba Geigy Ltd.) | 1 part |

Comparative Example 2-2

| | |
|---|---|
| 2-Ethylhexyl Acrylate | 98 parts |
| Acrylic Acid | 2 parts |
| Isocyanate Series Crosslinking Agent (Coronate L, made by Nippon Polyurethane Industry Co., Ltd.) | 2 parts |

Comparative Example 2-3

| | |
|---|---|
| Butyl Acrylate | 98 parts |
| Acrylic Acid | 2 parts |
| Isocyanate Series Crosslinking Agent (Coronate L, made by Nippon Polyurethane Industry Co., Ltd.) | 2 parts |

The average releasing forces and the maximum values at the beginning and after adhering and preserving (after 50° C.×1 day), the rolling initial tacking forces, and the retentive forces of the re-peeling pressure-sensitive adhesive tapes obtained in the examples and the comparative examples described above were measured using the foregoing adherend A by the methods described above and the results are shown in Table 2-1.

TABLE 2-1

| Properties | Releasing Rate (m/min.) | | Example 2-1 | Example 2-2 | Example 2-3 | Comparative Example 2-1 | Comparative Example 2-2 | Comparative Example 2-3 |
|---|---|---|---|---|---|---|---|---|
| Initial Releasing Force (g/25 mm) | 1 | Average | 150 | 170 | 280 | 200 | 80 | 80 |
| | | Maximum | 200 | 210 | 340 | 350 | 90 | 90 |
| | 10 | Average | 240 | 250 | 420 | 310 | 150 | 130 |
| | | Maximum | 280 | 300 | 530 | 520 | 170 | 150 |
| | 50 | Average | 400 | 450 | 260 | 130 | 240 | 190 |
| | | Maximum | 450 | 520 | 350 | 280 | 250 | 210 |
| Releasing Force After Adhering and Preserving (g/25 mm) | 1 | Average | 250 | 310 | 330 | 290 | 140 | 100 |
| | | Maximum | 310 | 390 | 400 | 450 | 15o | 120 |
| | 10 | Average | 330 | 430 | 420 | 360 | 210 | 160 |
| | | Maximum | 400 | 490 | 480 | 550 | 230 | 170 |
| | 50 | Average | 580 | 600 | 550 | 190 | 280 | 210 |
| | | Maximum | 650 | 650 | 620 | 390 | 290 | 230 |
| Rolling Initial Tacking Force (g/25 mm) | | | 180 | 80 | 220 | 150 | 110 | 20 |
| Retentive Force (min.) | | | 30 | ≧200 | 50 | ≧200 | 10 | 5 |

Practical Using Test

Paper diapers each having a back sheet as adherend A obtained by adhering and fixing thereto each of the re-peeling pressure-sensitive tapes obtained in the examples and the comparative examples were distributed to 15 mothers at 5 paper diapers per one mother, the practical usability was evaluated by the following standard, and the results are shown in Table 2-2.

A: Not less than 10 Persons in 15 persons evaluated as good.

B: Six to 9 persons in 15 persons evaluated as good.

C: Not more than 5 persons in 15 persons evaluated as good.

TABLE 2-2

Practical Using Test

| Example No. | Releas-ability | Break-age of Sheet | Detach-ing of Tape | Initial Adhesive Property | Re-adhesive Property | Total Evalua-tion |
|---|---|---|---|---|---|---|
| Example 2-1 | A | A | A | A | A | A |
| Example 2-2 | A | A | A | A | A | A |

TABLE 2-2-continued

Practical Using Test

| Example No. | Releas-ability | Break-age of Sheet | Detach-ing of Tape | Initial Adhesive Property | Re-adhesive Property | Total Evalua-tion |
|---|---|---|---|---|---|---|
| Example 2-3 | A | A | A | A | A | A |
| Comparative Example 2-1 | A | C | A | A | A | C |
| Comparative Example 2-2 | A | A | C | A | B | C |
| Comparative Example 2-3 | A | A | C | C | C | C |

Breaking Test of Adherend Sheet

Each of the re-peeling pressure-sensitive adhesive tapes obtained in the examples and the comparative examples was adhered to each of the following adherend sheets, the adhered adherend sheets directly after adhering under the atmosphere of 23° C. and the adhered adherend sheets after preserving for 12 hours under the conditions of 40° C. and 92% RH were prepared, and breaking test was carried out by releasing the re-peeling pressure-sensitive tape by a hand. The releasing rate in this case was from 10 to 50 meters/minute.

Also, the breaking strength was obtained by the method described above and the results are shown in Table 2-3.

Sheet A: The adherend A (thickness: 40 μm) used in the examples.

Sheet B: Thin type of sheet A (thickness: 20 μm).

Sheet C: Polyethylene/polyester composite fibrous nonwoven fabric (basis weight: 50 g/m$^2$).

Sheet D: Polypropylene nonwoven fabric (basis weight: 50 g/m$^2$).

Sheet E: Laminated type of sheet B and sheet D. (The pressure-sensitive tape is brought into contact with the sheet D side.)

Sheet F: Non-porous polyethylene film (thickness: 30 μm).

In addition, the result of the breaking test of each sheet was evaluated by the following standard.

A: Good

B: Elongation occurred

C: Broken

TABLE 2-3

| Sample of Adherend Sheet | Breaking Strength in MD Direction (kg/10 mm) | Example 2-1 | Example 2-2 | Example 2-3 | Comparative Examole 2-1 | Comparative Example 2-2 | Comparative Example 2-3 |
|---|---|---|---|---|---|---|---|
| A | 1.0 | A | A | A | C | A | A |
| B | 0.5 | A | A | A | C | A | A |
| C | 0.8 | A | A | A | C | A | A |
| D | 0.7 | A | A | A | C | A | A |
| E | 1.5 | A | A | A | C | A | A |
| F | 0.8 | A | A | A | C | A | A |

While the invention has been described in detail with reference to specific embodiments, it will be apparent to one skilled in the art that various changes and modifications can be made to the invention without departing from its spirit and scope.

What is claimed is:

1. A re-peeling pressure-sensitive adhesive tape or pressure-sensitive adhesive, which can be freely adhered to an adherend and can be repeatedly adhered and re-peeled without breaking the adherend, wherein said pressure-sensitive adhesive tape or pressure-sensitive adhesive satisfies all the following conditions:

(1) the average releasing force in each releasing rate in the case of releasing at a releasing rate of from 10 meters/minute to 100 meters/minute is from 50 g/25 mm to 1,000 g/25 mm, (2) the difference between the maximum value and the minimum value of the releasing force of the releasing chart pattern (the graph showing the releasing force to the change of time) obtained by the release in (1) is not larger than ⅔ of the average releasing force or not larger than 500 g/25mm, (3) the rolling initial tacking force is from 30 g/25 mm to 800 g/25 mm, and (4) the retentive force is at least 15 minutes under a load of 500 g;

wherein the re-peeling pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

2. The re-peeling pressure-sensitive adhesive tape or pressure-sensitive adhesive of claim 1, wherein the maximum releasing force in the releasing rate of from 50 meters/minute to 100 meters/minute is not more than the breaking strength of an adherend.

3. A fastening system, wherein a re-peeling pressure-sensitive adhesive tape or pressure-sensitive adhesive is re-peelably adhered to an adherend, said re-peeling pressure-sensitive adhesive tape or pressure-sensitive adhesive satisfying all the following conditions:

(1) the average releasing force in each releasing rate in the case of releasing at a releasing rate of from 10 meters/minute to 100 meters/minute is from 50 g/25 mm to 1,000 g/25 mm, (2) the difference between the maximum value and the minimum value of the releasing force of the releasing chart pattern (the graph showing the releasing force to the change of time) obtained by the release in (1) is not larger than $2/3$ of the average releasing force or not larger than 500 g/25 mm, (3) the rolling initial tacking force is from 30 g/25 mm to 800 g/25 mm, and (4) the retentive force is at least 15 minutes under a load of 500 g;

wherein the re-peeling pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

4. The fastening system of claim 3, wherein the breaking strength of the adherend is from 0.02 kg/10 mm to 10 kg/10 mm.

5. A fastening system, wherein a pressure-sensitive adhesive tape or pressure-sensitive adhesive is used as a fixing tape for an absorptive article, said re-peeling pressure-sensitive adhesive tape or pressure-sensitive adhesive satisfying all of the following conditions:

(1) the average releasing force in each releasing rate in the case of releasing at a releasing rate of from 10 meters/minute to 100 meters/minute is from 50 g/25 mm to 1,000 g/25 mm, (2) the difference between the maximum value and the minimum value of the releasing force of the releasing chart pattern (the graph showing the releasing force to the change of time) obtained by the release in (1) is not larger than $2/3$ of the average releasing force or not larger than 500 g/25 mm, (3) the rolling initial tacking force is from 30 g/25 mm to 800 g/25 mm, and (4) the retentive force is at least 15 minutes under a load of 500 g;

wherein the pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

6. A fastening system, wherein a pressure-sensitive adhesive tape or pressure-sensitive adhesive is used as a fixing tape for a packaged article, said re-peeling pressure-sensitive adhesive tape or pressure-sensitive adhesive satisfying all of the following conditions:

(1) the average releasing force in each releasing rate in the case of releasing at a releasing rate of from 10 meters/minute to 100 meters/minute is from 50 g/25 mm to 1,000 g/25 mm, (2) the difference between the maximum value and the minimum value of the releasing force of the releasing chart pattern (the graph showing the releasing force to the change of time) obtained by the release in (1) is not larger than $2/3$ of the average releasing force or not larger than 500 g/25 mm, (3) the rolling initial tacking force is from 30 g/25 mm to 800 g/25 mm, and (4) the retentive force is at least 15 minutes under a load of 500 g;

wherein the pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

7. A re-peeling pressure-sensitive adhesive tape or pressure-sensitive adhesive, which can be freely adhered to an adherend and can be repeatedly adhered and re-peeled without breaking the adherend, wherein said pressure-sensitive adhesive tape or pressure-sensitive adhesive satisfies all the following conditions:

(1) the average releasing force in each releasing rate in the case of releasing at a releasing rate of from 1 meter/minute to 50 meters/minute is from 100 g/25 mm to 1,000 g/25 mm, (2) in the relation between the releasing force and the releasing rate after adhering to an adherend and preserving, the peak of the releasing force does not exist in the range of the releasing rate of not higher than 50 meters/minute, (3) the rolling initial tacking force is from 30 g/25 mm to 800 g/25 mm, and (4) the retentive force is at least 15 minutes under a load of 500 g;

wherein the re-peeling pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

8. The re-peeling pressure-sensitive adhesive tape or pressure-sensitive adhesive of claim 7, wherein the average releasing force in each releasing rate in the case of releasing at a releasing rate of from 1 meter/minute to 50 meters/minute is at least 100 g/25 mm and the maximum releasing force is not more than the breaking strength of an adherend.

9. A fastening system, wherein a re-peeling pressure-sensitive adhesive tape or pressure-sensitive adhesive re-peelably adheres to an adherend, said re-peeling pressure-sensitive adhesive tape or pressure-sensitive adhesive satisfying all of the following conditions:

(1) the average releasing force in each releasing rate in the case of releasing at a releasing rate of from 1 meter/minute to 50 meters/minute is from 100 g/25 mm to 1,000 g/25 mm, (2) in the relation between the releasing force and the releasing rate after adhering to an adherend and preserving, the peak of the releasing force does not exist in the range of the releasing rate of not higher than 50 meters/minute, (3) the rolling initial tacking force is from 30 g/25 mm to 800 g/25 mm, and (4) the retentive force is at least 15 minutes under a load of 500 g;

wherein the pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

10. The fastening system of claim 9, wherein the breaking strength of the adherend is from 0.02 kg/10 mm to 10 kg/10 mm.

11. A fastening system, wherein a pressure-sensitive adhesive tape or pressure-sensitive adhesive is used as a fixing tape for an absorptive article, said re-peeling pressure-sensitive adhesive tape or pressure-sensitive adhesive satisfying all of the following conditions:

(1) the average releasing force in each releasing rate in the case of releasing at a releasing rate of from 1 meter/minute to 50 meters/minute is from 100 g/25 mm to 1,000 g/25 mm, (2) in the relation between the releasing force and the releasing rate after adhering to an adherend and preserving, the peak of the releasing force does not exist in the range of the releasing rate of not higher than 50 meters/minute, (3) the rolling initial tacking force is from 30 g/25 mm to 800 g/25 mm, and (4) the retentive force is at least 15 minutes under a load of 500 g;

wherein the pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

12. A fastening system, wherein a pressure-sensitive adhesive tape or pressure-sensitive adhesive is used as a fixing tape for a packaged article, said re-peeling pressure-sensitive adhesive tape or pressure-sensitive adhesive satisfying all the following conditions:

(1) the average releasing force in each releasing rate in the case of releasing at a releasing rate of from 1 meter/minute to 50 meters/minute is from 100 g/25 mm to 1,000 g/25 mm, (2) in the relation between the releasing force and the releasing rate after adhering to an adherend and preserving, the peak of the releasing force does not exist in the range of the releasing rate of not higher than 50 meters/minute, (3) the rolling initial tacking force is from 30 g/25 mm to 800 g/25 mm, and (4) the retentive force is at least 15 minutes under a load of 500 g;

wherein the pressure-sensitive adhesive tape or pressure-sensitive adhesive contains an elastomer which is a block copolymer composed of a polymer block A mainly composed of a vinyl aromatic compound and a polymer block B mainly composed of a conjugated diene compound;

wherein the content of the polymer block A is at least 17% by weight and the coupling ratio is at least 50%; and wherein the increase of the adhesive force after adhering to an adherend and preserving is not more than 4 times the initial adhesive force.

* * * * *